United States Patent [19]

Nagasawa et al.

[11] Patent Number: 6,017,724
[45] Date of Patent: Jan. 25, 2000

[54] OXIDOREDUCTASE AND METHOD FOR PREPARING 3-(P-HYDROXYPHENYL)-2-PROPENOL DERIVATIVES OR THE LIKE USING THE ENZYME

[75] Inventors: Toru Nagasawa, Gifu; Hiroshi Morita, Kawasaki; Yumiko Iwasawa, Kanagawa-ken, all of Japan

[73] Assignee: Chisso Corporation, Osaka-fu, Japan

[21] Appl. No.: 09/137,829

[22] Filed: Aug. 21, 1998

Related U.S. Application Data

[63] Continuation of application No. PCT/JP97/00518, Feb. 24, 1997, abandoned.

[30] Foreign Application Priority Data

Feb. 23, 1996 [JP] Japan ................................ 8-061936
Sep. 4, 1996 [JP] Japan ................................ 8-253937
Oct. 3, 1996 [JP] Japan ................................ 8-281907

[51] Int. Cl.[7] .............................. C12Q 1/26; C12N 9/02; C12P 7/24
[52] U.S. Cl. .............................. 435/25; 435/189; 435/147
[58] Field of Search ...................... 435/189, 25; 438/147

[56] References Cited

FOREIGN PATENT DOCUMENTS 0583687  2/1994  European Pat. Off. .
5-227980  9/1993  Japan .
WO95/02062  1/1995  WIPO .

OTHER PUBLICATIONS

Fraaije et al., "Substrate specificity of flavin–dependent vanillyl–alcohol oxidase from *Penicillium simplicissimum*, Evidence for the production of 4–hydroxycinnamyl alcohols from 4–allylphenols", Eur. J. Biochem. 234, 271–277 (1995).

Tadasa, "Degradation of Eugenol by a Microorganism", Agric. Biol. Chem., 41 (6), 925–929, 1977.

Tadasa et al., "Initial Steps of Eugenol Degradation Pathway of a Microorganism", Agric. Biol. Chem. 47 (11), 2639–2640, 1983.

*Primary Examiner*—Eggerton A. Campbell
*Assistant Examiner*—Devesh Srivastava
*Attorney, Agent, or Firm*—Wenderoth, Lind & Ponack, L.L.P.

[57] ABSTRACT

The present invention relates to a novel enzyme which is derived from bacterial cells of a strain belonging to the genus *Pseudomonas fluorescens* and which catalyzes a reaction for oxidizing substrates such as p-hydroxytoluene derivatives and p-alkylphenol derivatives as well as a method for preparing, for instance, 3-(p-hydroxyphenyl)-2-propenol derivatives, p-hydroxybenzaldehyde derivatives, p-alkylphenol derivatives and optically active S(-)-1-(4-hydroxyphenyl) alcohol derivatives, using the enzyme.

9 Claims, No Drawings

OXIDOREDUCTASE AND METHOD FOR PREPARING 3-(P-HYDROXYPHENYL)-2-PROPENOL DERIVATIVES OR THE LIKE USING THE ENZYME

This application is a continuation of International Application No. PCT/JP97/00518 filed Feb. 24, 1997, now abandoned as to the United States.

TECHNICAL FIELD

The present invention relates to a novel enzyme which is derived from bacterial cells of a strain belonging to the genus Pseudomonas fluorescens and which catalyzes a reaction for oxidizing substrates such as p-hydroxytoluene derivatives and p-alkylphenol derivatives as well as a method for preparing, for instance, 3-(p-hydroxyphenyl)-2-propenol derivatives, p-hydroxybenzaldehyde derivatives, p-alkylphenol derivatives and optically active S(-)-1-(4-hydroxyphenyl) alcohol derivatives, using the enzyme.

PRIOR ART

There has never been reported any oxidoreductase which can catalyze a reaction wherein the double bond, at the α-position, of a substrate such as a p-allylphenol derivative represented by eugenol is moved to the position next to the α-position and a hydroxyl group is added to the position, in the presence of water and an electron acceptor and accordingly, there has not yet been known any method for preparing a 3-(p-hydroxyphenyl)-2-propenol derivative represented by coniferyl alcohol, while making use of such an enzyme. Moreover, there has not been reported any reaction catalyzed by such an enzyme.

In addition, coniferyl alcohol as one of 3-(p-hydroxyphenyl)-2-propenol derivatives has been expected as a substance capable of being widely used, i.e., as a raw material for, for instance, medicines, cosmetics, perfumes, agricultural chemicals, food additives, feed supplements and liquid crystals and it has been known that this coniferyl alcohol can be prepared as a by-product in the step for producing vanillin. However, the amount of coniferyl alcohol produced by the step is low. Therefore, coniferyl alcohol is very expensive and this has in turn prevented wide use of the compound.

Various attempts have been made to produce vanillin-related substances by acting a microorganism on cheaper eugenol (Japanese Un-Examined Patent Publication (hereinafter referred to as "J.P. KOKAI") No. Hei 5-227980; Agricultural Biological Chemistry, 1977, 41, pp. 925–929; ibid., 1983, 47, pp. 2639–2640), but any of them have failed in efficient production of coniferyl alcohol, although they can produce vanillin or vanillic acid.

There has not been proposed, at all, any oxidoreductase which can catalyze a reaction wherein a p-alkylphenol derivative is oxidized in the presence of water and an electron acceptor to produce an optically active 1-(4-hydroxyphenyl)alcohol derivative in high efficiency.

The optically active 1-(4-hydroxyphenyl)alcohol derivatives has been expected as a substance capable of being widely used, i.e., as a raw material for synthesizing, for instance, medicines, cosmetics, perfumes, agricultural chemicals, food additives, feed supplements and liquid crystals. In particular, the compound is used as a chiral synthon in synthesis of a vasodilator.

DISCLOSURE OF THE INVENTION

An object of the present invention is to provide a novel oxidoreductase which can catalyze a reaction wherein the double bond, at the α-position, of a substrate such as eugenol is moved to the position next thereto and a hydroxyl group is added to the α-position, in the presence of water and an electron acceptor and a method for preparing useful compounds including coniferyl alcohol in high efficiency while using the enzyme. Another object of the present invention is to provide a method for preparing compounds such as 3-(p-hydroxyphenyl)-2-propenol derivatives, p-hydroxybenzaldehyde derivatives and optically active 1-(4-hydroxyphenyl)alcohol derivatives, while making use of various organic reactions which are catalyzed by the enzyme.

According to the present invention, there is thus provided an oxidoreductase having the following characteristic properties:

(1) Operation: The enzyme can produce coniferyl alcohol by moving the double bond at the α-position of eugenol to the position next thereto and adding a hydroxyl group to the position in the presence of water.

(2) Substrate Specificity: The enzyme acts on the compounds represented by the general formulas (1-a), (1-b), (1-c), (1-c') and (1-d) to give the compounds represented by the general formulas (2-a), (2-b), (2-c), (2-c') and (2-d) respectively.

(3) Affinity for Substrate: Michaelis constants of the enzyme for eugenol and phenazine methosulfate correspond to substrate concentrations of 1.75 mM and 0.4 mM, respectively.

(4) Optimum pH: The enzyme has an optimum pH of about 5.5.

(5) Optimum Temperature: 50° C.

(6) Stable pH Range: The enzyme is stable within the pH range of from 5 to 9 for the treatment at 30° C. for 30 minutes.

(7) Effects of Various Kinds of Metal Salts on the Enzyme: The activity of the enzyme is considerably inhibited by salts of divalent iron, copper, silver and mercury.

(8) Effects of Various Kinds of Inhibitors on the Enzyme: The activity of the enzyme is inhibited by p-(chloromercuri) benzoic acid and phenylhydrazine.

(9) Molecular Weight: The enzyme is a heterodimer having a molecular weight of 68,600 and consisting of an α-subunit having a molecular weight of 10,400 and a β-subunit having a molecular weight of 58,200.

According to the present invention, there is also provided an oxidoreductase having the following characteristic properties.

An oxidoreductase which can be prepared by cultivating a strain belonging to the genus Pseudomonas fluorescens in a nutritional culture medium containing eugenol and extracting the enzyme produced in the bacterial cells of the strain and which can catalyze at least the reactions represented by the following reaction schemes A, B and C:

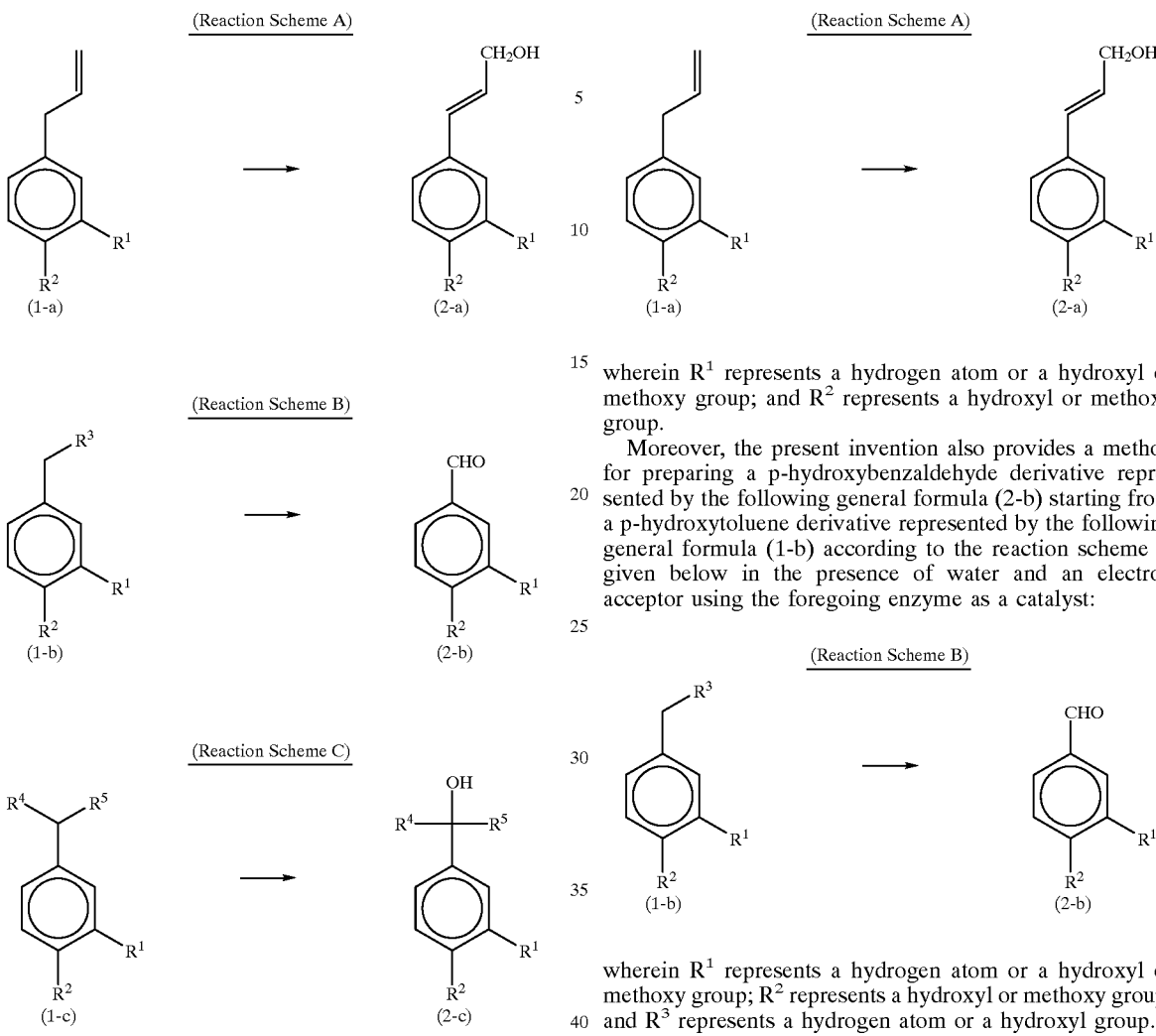

wherein R¹ represents a hydrogen atom or a hydroxyl or methoxy group; R² represents a hydroxyl or methoxy group; R³ represents a hydrogen atom or a hydroxyl group; R⁴ represents a hydrogen atom or a methyl group; and R⁵ represents an alkyl group having 1 to 10 carbon atoms or an aminomethyl group.

The enzyme of the present invention is preferably those capable of catalyzing asymmetry-inducing reactions represented by Scheme C wherein R⁴ is a hydrogen atom.

The enzyme of the present invention is preferably those defined above wherein the strain belonging to the genus Pseudomonas fluorescens is Pseudomonas fluorescens E118 (FERM P-15185).

The present invention further provides a method for preparing a 3-(p-hydroxyphenyl)-2-propenol derivative represented by the following general formula (2-a) starting from a p-allylphenol derivative represented by the following general formula (1-a) according to the reaction scheme A given below in the presence of water and an electron acceptor using the foregoing enzyme as a catalyst:

wherein R¹ represents a hydrogen atom or a hydroxyl or methoxy group; and R² represents a hydroxyl or methoxy group.

Moreover, the present invention also provides a method for preparing a p-hydroxybenzaldehyde derivative represented by the following general formula (2-b) starting from a p-hydroxytoluene derivative represented by the following general formula (1-b) according to the reaction scheme B given below in the presence of water and an electron acceptor using the foregoing enzyme as a catalyst:

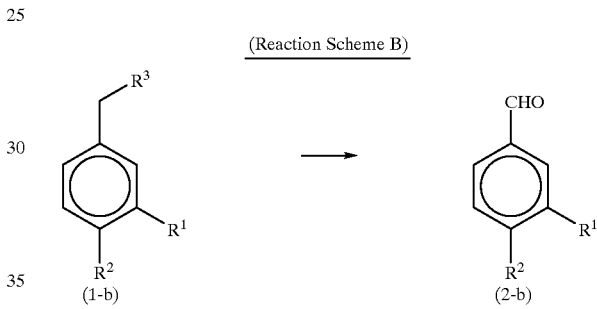

wherein R¹ represents a hydrogen atom or a hydroxyl or methoxy group; R² represents a hydroxyl or methoxy group; and R³ represents a hydrogen atom or a hydroxyl group.

In addition, the present invention likewise provides a method for preparing a p-hydroxybenzyl alcohol derivative represented by the following general formula (2-c) starting from a p-alkylphenol derivative represented by the following general formula (1-c) according to the reaction scheme C given below in the presence of water and an electron acceptor using the foregoing enzyme as a catalyst:

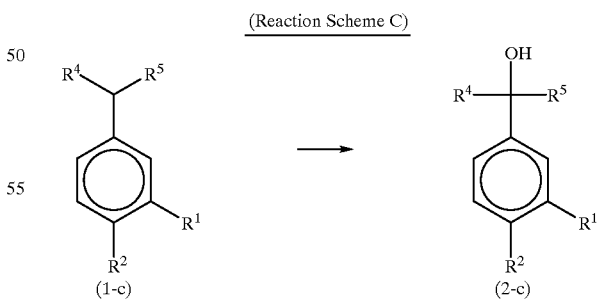

wherein R¹ represents a hydrogen atom or a hydroxyl or methoxy group; R² represents a hydroxyl or methoxy group; R⁴ represents a hydrogen atom or a methyl group; and R⁵ represents an alkyl group having 1 to 10 carbon atoms or an aminomethyl group.

Furthermore, the present invention also provides a method for preparing an optically active hydroxybenzyl alcohol derivative represented by the following general formula (2-c') starting from an alkylphenol derivative represented by the following general formula (1-c') according to the reaction scheme C' given below in the presence of water and an electron acceptor using the foregoing enzyme as a catalyst:

(Reaction Scheme C')

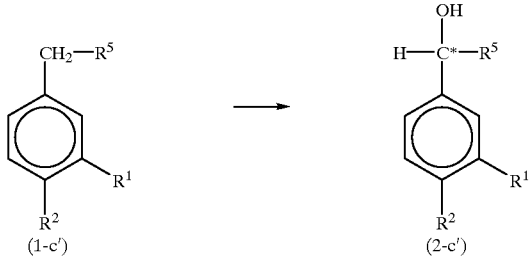

wherein $R^1$ and $R^2$ each independently represents a hydrogen atom or a hydroxyl or methoxy group, provided that $R^1$ and $R^2$ do not simultaneously represent a hydrogen atom; and $R^5$ represents an alkyl group having 1 to 10 carbon atoms or an aminomethyl group.

The present invention likewise provides a method for preparing the compound represented by the following general formula (2-d) starting from the compound represented by the following general formula (1-d) according to the reaction scheme D given below in the presence of water and an electron acceptor using the foregoing enzyme as a catalyst:

(Reaction Scheme D)

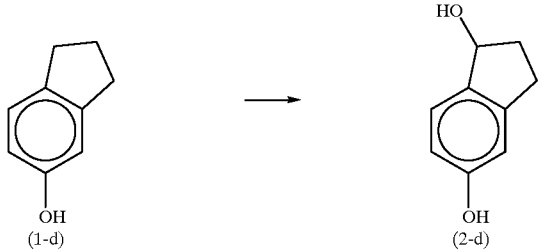

BEST MODE FOR CARRYING OUT THE INVENTION

To prepare the enzyme of the present invention, a strain belonging to Pseudomonas fluorescens, which is a bacterial cell capable of producing the enzyme, is aerobically cultivated in a culture medium containing eugenol. The culture medium may be any one which contains eugenol and allows the bacterial cell to grow, but preferably used are those containing 0.1 to 0.4% (v/v) of eugenol, 0.5 to 3% (w/v) of sucrose, 0.05 to 0.2% (w/v) of peptone, 0.01 to 0.1% (w/v) of magnesium sulfate heptahydrate, 0.05 to 0.2% (w/v) of ferrous sulfate heptahydrate, 0.1 to 1% (w/v) of yeast extract and 0.05 to 0.2% (v/v) of a mixed solution of metal salts and having a pH ranging from 6.5 to 8.0. The mixed solution of metal salts is preferably a solution obtained by dissolving, in one liter of deionized water, 0.4 g of calcium chloride dihydrate, 0.3 g of boric acid, 0.04 g of copper sulfate pentahydrate, 0.1 g of potassium iodide, 0.4 g of manganese sulfate heptahydrate and 0.2 g of sodium molybdate dihydrate. The cultivation of the strain is carried out at 20 to 35° C. for 18 to 72 hours according to the aeration agitation culture. The bacterial cells obtained by, for instance, centrifugation or filtration of the resulting culture medium are suspended in a 1M potassium phosphate buffer (pH 7.0), followed by treating the bacterial cells with an ultrasonic disintegrator or a cell crusher to disrupt the cells and to thus obtain a crude enzyme solution.

The resulting crude enzyme solution is treated by the salting-out method with ammonium sulfate and/or various kinds of column chromatography methods such as ion-exchange, gel filtration and hydrophobic chromatography methods to thus give a highly purified enzyme sample. Thus, a purified enzyme sample can be obtained, which is recognized to be a single enzyme in the SDS-polyacrylamide-gel electrophoresis. Enzyme-chemical properties of this enzyme (the enzyme of the invention) will be described below.

[Enzyme-Chemical Properties of The Enzyme]

(1) Operations: The enzyme has such an effect that it produces coniferyl alcohol by moving the double bond at the α-position of eugenol to the position next thereto and adding a hydroxyl group to the α-position in the presence of water.

(2) Substrate Specificity: The enzyme acts on the compounds represented by the foregoing general formulas (1-a), (1-b), (1-c), (1-c') and (1-d) to give the compounds represented by the foregoing general formulas (2-a), (2-b), (2-c), (2-c') and (2-d) respectively. There may be used such an electron acceptor as cytochrome C, 2,6-dichloroindophenol and phenazine methosulfate.

(3) Affinity for Substrate: Michaelis constants of the enzyme for eugenol and phenazine methosulfate correspond to substrate concentrations of 1.75 mM and 0.4 mM respectively.

(4) Optimum pH: about 5.5.

(5) Optimum Temperature: 50° C.

(6) Stable pH Range: The enzyme is stable within the pH range of from 5 to 9 for the treatment at 30° C. for 30 minutes.

(7) Effects of Various Kinds of Metal Salts on the Enzyme: The activity of the enzyme is considerably inhibited by salts of divalent iron, copper, silver and mercury, as will be seen from the following Table 1:

TABLE 1

Effects of Various Kinds of Metal Salts on the Enzyme

| Metal Salts | Relative Activity (%) |
|---|---|
| No Addition | 100 |
| NaCl | 99.8 |
| $CoCl_2 \cdot H_2O$ | 89.8 |
| $FeCl_2 \cdot nH_2O$ | 28.9 |
| $FeCl_3 \cdot 6H_2O$ | 76.9 |
| $MgCl_2 \cdot 6H_2O$ | 96.2 |
| $CaCl_2$ | 113 |
| $NiCl_2 \cdot 6H_2O$ | 94.2 |
| $ZnCl_2$ | 113 |
| $MnCl_2 \cdot 4H_2O$ | 82.7 |
| $SnCl_2 \cdot 2H_2O$ | 100 |
| $Al_2(SO_4)_3 \cdot 18H_2O$ | 102 |
| $CuCl_2 \cdot 2H_2O$ | 6.75 |
| $Ag_2SO_4$ | 1.10 |
| $HgCl_2$ | 11.1 |
| $BaCl_2 \cdot 2H_2O$ | 105 |
| $CdCl_2 \cdot 2.5H_2O$ | 91.5 |
| $PbCl_2$ | 90.4 |

(8) Effects of Various Kinds of Inhibitors on the Enzyme: The activity of the enzyme is inhibited by p-(chloromercuri) benzoic acid and phenylhydrazine, as will be seen from Table 2 given below:

TABLE

Effects of Various Kinds of Inhibitors on the Enzyme

| Inhibitor | Relative Activity (%) |
|---|---|
| no inhibitor | 100 |
| 5,5'-dithiobis(2-nitro benzoic acid) | 79.8 |
| N-ethylmaleimide | 105 |
| iodoacetic acid | 93.9 |
| p-(chloromercuri) benzoic acid | 41.8 |
| hydroxylamine | 84.4 |
| phenylhydrazine | 46.2 |
| semicarbazide | 93.9 |
| cysteamine | 110 |
| L-penicillamine | 77.1 |
| D-penicillamine | 82.4 |
| D-cycloserine | 96.6 |
| o-phenanthroline | 115 |
| α,α'-dipyridyl | 113 |
| thirone | 100 |
| EDTA | 92.0 |
| 8-hydroxyquinoline | 92.2 |
| sodium azide | 87.0 |
| potassium cyanide | 72.5 |
| diethyldithiocarbamate | 87.3 |
| dithiothreitol | 95.5 |
| 2-mercaptoethanol | 87.3 |
| L-ascorbic acid | 69.3 |
| $Na_2S_2O_4$ | 97.6 |
| $H_2O_2$ | 94.8 |
| ammonium persulfate | 100 |
| cuprizone | 95.1 |
| EPNP | 83.4 |
| PMSF | 83.9 |

EDTA: ethylenediaminetetraacetic acid
EPNP: 1,2-epoxy-3-(p-nitrophenoxy)propane
PMSF: phenylmethanesulfonyl fluoride (9) Molecular Weight: The enzyme is initially assumed to be a dimer consisting of two identical subunits since it has a molecular weight of 59,000 and 110,000 as determined by SDS-polyacrylamide-gel electrophoresis and ultracentrifugal analysis, respectively, but it has become clear, after more precise analysis using TOF-MS, that the enzyme is a heterodimer having a molecular weight of 68,600 and consisting of an α-subunit having a molecular weight of 10,400 and a β-subunit having a molecular weight of 58,200.

(10) Determination of Enzyme Activity:

To a test tube containing a reaction solution for enzyme-activity determination comprising 50 μl of a 200 mM solution of eugenol in n-octane, 200 μl of a 50 mM aqueous solution of phenazine methosulfate, 50 μl of a 1M potassium phosphate buffer (pH 7.0) and 675 μl of deionized water, there was added 25 μl of an enzyme solution, followed by shaking at 30° C. for 20 minutes, termination of the reaction by addition of 1 ml of methanol, subsequent centrifugation of the resulting reaction solution, subjecting the resulting supernatant to high performance liquid chromatography to thus detect the peak of coniferyl alcohol and quantify the same.

The high performance liquid chromatography is performed using an ODS C18 column having a size of 4.6×150 mm, while developing by passing a methanol : deionized water : acetic acid (=45:52:3 (volume ratio)) mixed solvent as an eluent at a flow rate of 1.0 ml/min through the column to detect the absorbance at 280 nm. The peak appearing near 3.6 minutes which corresponds to the retention time of the standard coniferyl alcohol is ascribed to coniferyl alcohol.

One unit of the activity of the enzyme is defined to be that required for producing 1 μM of coniferyl alcohol per one minute.

A method for preparing the compound represented by the general formula (2-a) using the enzyme will be described below while taking coniferyl alcohol as an example.

A dilute sulfuric acid solution or aqueous ammonia was dropwise added to the foregoing reaction solution for enzyme-activity determination from which the buffer is omitted (i.e., a solution comprising 50 μl of a 200 mM solution of eugenol in n-octane, 200 μl of a 50 mM aqueous solution of phenazine methosulfate and 675 μl of deionized water) to adjust the pH thereof from 5 to 7 and the resulting mixture is stirred at a temperature ranging from 25 to 55° C. for 15 to 180 minutes. After the completion of the reaction, the coniferyl alcohol is extracted from the reaction solution with an organic solvent such as ethyl acetate, chloroform, methylene chloride or ethyl ether, followed by purification thereof by a means such as silica gel chromatography, reverse phase liquid chromatography or vacuum distillation, optional discoloration with active carbon and vacuum drying to give colorless coniferyl alcohol powder.

In the same manner, there can be prepared the compound represented by Formula (2-a) from that represented by Formula (1-a); the compound represented by Formula (2-b) from that represented by Formula (1-b); the compound represented by Formula (2-c) from that represented by Formula (1-c); the compound represented by Formula (2-c') from that represented by Formula (1-c'); the compound represented by Formula (2-d) from that represented by Formula (1-d), respectively. In this connection, if $R^4$ in Formula (1-c) is a hydrogen atom, the reaction is an asymmetry-inducing reaction and provides an optically active compound.

The water used in the preparation of the foregoing compounds by the method of the present invention serves not only as a solvent for the reaction and an oxygen atom-supply source, but also as an electron donor required for the enzyme reaction.

In the present invention, the amounts of water and the electron acceptor each is identical to or greater than the molar number of the substrate to be reacted. In general, water is used in large excess since it is also used as a solvent.

EXAMPLE

Then the present invention will more specifically be described below, but the present invention is not restricted to these Examples.

Example 1

Pseudomonas fluorescens E118 strain, FERM P-15185, was cultivated in 20 l of a culture medium comprising 0.15% (v/v) of eugenol, 1% (w/v) of sucrose, 0.1% (w/v) of peptone, 0.2% (w/v) of dipotassium phosphate, 0.05% of magnesium sulfate heptahydrate, 0.03% (w/v) of yeast extract, 0.1% (w/v) of ferrous sulfate heptahydrate and 0.1% (v/v) of a mixed solution of metal salts and having a pH of 7.0, for 54 hours according to the aeration agitation culture. The mixed solution of metal salts used was a solution obtained by dissolving, in one liter of deionized water, 0.4 g of calcium chloride dihydrate, 0.3 g of boric acid, 0.04 g of copper sulfate pentahydrate, 0.1 g of potassium iodide, 0.4 g of manganese sulfate heptahydrate and 0.2 g of sodium molybdate dihydrate. The culture medium was centrifuged to give bacterial cells, then the cells were washed with physiological saline and suspended in 300 ml of a 10 mM potassium phosphate buffer (pH 7.0). The enzyme of the present invention was extracted from this suspension of the bacterial cells and purified by the method described below. Table 3 shows the scheme for purification.

The suspension of the cells was treated with an ultrasonic disintegrator to break them and centrifuged to give 2140 mg (total activity: 270 units) of a supernatant as a cell-free extract. To the extract, there was added ammonium sulfate to obtain 1310 mg (total activity: 228 units) of a 30 to 50% (w/v) ammonium sulfate-saturated fraction. This fraction was treated in a column packed with DEAE-Sephacell (available from Pharmacia) to obtain 58 mg (total activity: 115 units) of an active fraction. Ammonium sulfate was added to the active fraction to give 37.2 mg (total activity: 102 units) of a 40 to 80% (w/v) ammonium sulfate-saturated fraction. This fraction was chromatographed using, in order, columns packed with Phenyl Sepharose, DEAE-Sepharose, Octyl Sepharose (all of them are available from Pharmacia) to ultimately obtain 0.4 mg (total activity: 12.1 unit) of an enzyme sample. This sample was recognized to be a single enzyme in the SDS-polyacrylamide-gel electrophoretic analysis.

In this respect, the specific activity was finally increased to 209 fold that observed for the cell-free extract and the rate of recovery was found to be 4.5%.

TABLE 3

Purification Scheme for the Enzyme

| | Amt. of Tot. Pro- tein, mg | Spec. Act. Unit/mg | Tot. Act. Unit | Rate of Recovery % | Purity Fold |
|---|---|---|---|---|---|
| Cell-free Extract | 2140 | 0.13 | 270 | 100 | 1.0 |
| $(NH_4)_2SO_4$ Salting Out, 30–50% | 1310 | 0.17 | 228 | 84.4 | 1.4 |
| DEAE-Sephacell | 58.0 | 1.98 | 115 | 42.6 | 15.7 |
| $(NH_4)_2SO_4$ Salting Out, 40–80% | 37.2 | 2.74 | 108 | 37.8 | 21.7 |
| Phenyl Sepharose | 11.8 | 6.88 | 81.6 | 30.2 | 54.6 |
| DEAE-Sepharose | 1.98 | 14.1 | 27.5 | 10.3 | 112 |
| Octyl Sepharose | 0.46 | 26.3 | 12.1 | 4.48 | 209 |

Example 2

An enzyme solution (25 ml, 20 units) prepared according to the procedures of Example 1 and obtained after the second salting-out with ammonium sulfate was added to a reaction container equipped with a reflux condenser and containing 50 ml of a 200 mM solution of eugenol in n-octane, 200 ml of a 50 mM phenazine methosulfate aqueous solution and 725 ml of deionized water and stirred at 50° C. for 2 hours while maintaining the pH to 5.5 by automatic and dropwise addition of diluted sulfuric acid. The reaction solution was extracted with 800 ml of ethyl acetate, the resulting ethyl acetate phase was concentrated using a rotary evaporator up to 20 ml and then treated by a silica gel column. Fractions eluted by a 1:1 methanol: chloroform mixed solvent were collected and then vacuum-dried at room temperature to give 1.6 g of colorless powder having a melting point of 74° C. The yield thereof was found to be 89%. This powder was subjected to the GCMS analysis to determine the parent peak. The latter was found to be 180 m/z and was in agreement with that of the standard coniferyl alcohol. The infrared absorption spectra were likewise consistent with those observed for the standard coniferyl alcohol and consequently, the colorless powder was identified to be coniferyl alcohol.

Example 3

The procedures similar to those used in Example 2 were repeated except for using each substrate listed in the following Tables 4 to 5 to form each corresponding product. Each product was identified by, for instance, the GCMS analysis and the IR absorption spectrometric analysis. The optical activity of each product was determined by the high performance liquid chromatography while using a 9:1 n-hexane/n-propanol mixed solvent as a mobile phase and an ultraviolet light detector and an optical rotatory detector for the detection of peaks. The activity of the product against each substrate is expressed in terms of a relative activity with respect to the activity observed when eugenol is used as a substrate, which is defined to be 100.

TABLE 4

| Substrate | | | | Product | | | Relative | |
|---|---|---|---|---|---|---|---|---|
| Formula | $R^1$ | $R^2$ | $R^3$ | Formula | $R^1$ | $R^2$ | Activity | |
| (1-a) | $OCH_3$ | OH | — | (2-a) | $OCH_3$ | OH | 100 | Example 2 |
| (1-a) | $OCH_3$ | $OCH_3$ | — | (2-a) | $OCH_3$ | $OCH_3$ | 42.5 | |
| (1-b) | H | OH | H | (2-b) | H | OH | 7.93 | Substrate: p-cresol |
| (1-b) | H | OH | OH | (2-b) | H | OH | 122 | |
| (1-b) | $OCH_3$ | OH | OH | (2-b) | $OCH_3$ | OH | 90.4 | Product: vanillin |

TABLE 5

| Substrate/Formula (1-c/1-c') | | | | Product/Formula (2-c/2-c') | | | | | |
|---|---|---|---|---|---|---|---|---|---|
| $R^1$ | $R^2$ | $R^4$ | $R^5$ | $R^1$ | $R^2$ | $R^4$ | $R^5$ | Steric Conformation/ ee (%) | Relative Activity |
| H | OH | H | $CH_3$ | H | OH | H | $CH_3$ | S(−)/91.5 | 78.0 |
| H | OH | H | $C_2H_5$ | H | OH | H | $C_2H_5$ | S(−)/91.1 | 72.8 |
| H | OH | H | $C_3H_7$ | H | OH | H | $C_3H_7$ | S(−)/90.8 | 66.4 |

TABLE 5-continued

| Substrate/Formula (1-c/1-c') | | | | Product/Formula (2-c/2-c') | | | | Steric Conformation/ ee (%) | Relative Activity |
|---|---|---|---|---|---|---|---|---|---|
| $R^1$ | $R^2$ | $R^4$ | $R^5$ | $R^1$ | $R^2$ | $R^4$ | $R^5$ | | |
| H | OH | H | $C_5H_{11}$ | H | OH | H | $C_5H_{11}$ | S(−)/90< | 38.1 |
| OH | H | H | $CH_3$ | OH | H | H | $CH_3$ | S(−)/90< | 18.8 |
| H | OH | $CH_3$ | $CH_3$ | H | OH | $CH_3$ | $CH_3$ | —/— | 6.25 |
| H | OH | $CH_3$ | $C_2H_5$ | H | OH | $CH_3$ | $C_2H_5$ | | 12.1 |
| OH | OH | H | $CH_2NH_2$ | OH | OH | H | $CH_2NH_2$ | | 10< |

Example 4

Furthermore, the enzyme of the present invention was active in the reaction represented by the following reaction scheme D and could produce the compound of Formula (2-d) starting from the substrate of Formula (1-d) in the same manner used in Example 2. In addition, this reaction was confirmed to be an asymmetry-inducing reaction.

(Reaction Scheme D)

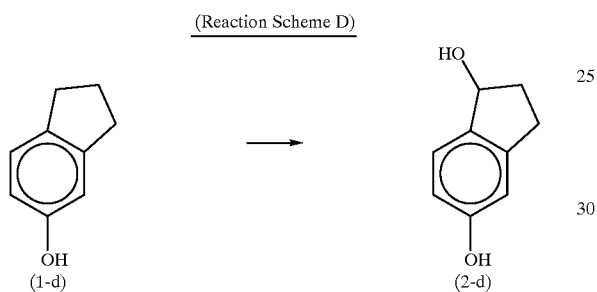

[Industrial Applicability]

The present invention relates to an enzyme which catalyzes a reaction for producing, for instance, an unsaturated alcohol, wherein the double bond of a substrate at the α-position is rearranged and a hydroxyl group is added to the α-position. Therefore, the use of such an enzyme permits efficient production of various kinds of 3-(p-hydroxyphenyl)-2-propenol derivatives, p-hydroxybenzaldehyde derivatives and optically active 1-(4-hydroxyphenyl)alcohol derivatives including coniferyl alcohol.

[Description of the Deposited Microorganism]
Name of Depository: National Institute of Bioscience and Human-Technology, Agency of Industrial Science and Technology in Ministry of International Trade and Industry, Japan
Address (Residence): 1-3, Higashi 1-Chome, Tsukuba-City, Ibaraki, Japan
Deposition Date: Heisei 7 (1995), September 14
Accession No. FERM P-15185

What is claimed is:

1. An isolated oxidoreductase having the following properties:
   (1) Operation: The enzyme can produce coniferyl alcohol by moving the double bond at the α-position of eugenol to the position next thereto and adding a hydroxyl group to the α-position in the presence of water;
   (2) Substrate Specificity: The enzyme acts on the compounds represented by the general formulas (1-a), (1-b), (1-c), (1-c') and (1-d) to give the compounds represented by the general formulas (2-a), (2-b), (2-c), (2-c') and (2-d) respectively;

(Reaction Scheme A)

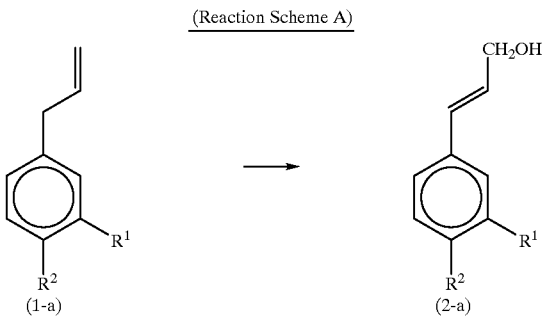

(Reaction Scheme B)

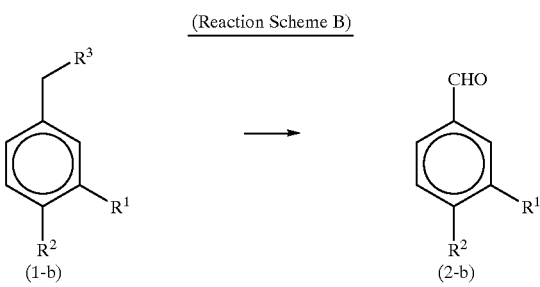

2. An isolated enzyme which is preparable by cultivating a strain belonging to the genus *Pseudomonas fluorescens* in a nutritional culture medium containing eugenol and extracting the enzyme produced in the bacterial cells of the strain and which catalyzes at least the reactions represented by the following reaction schemes A, B and C:

(Reaction Scheme A)

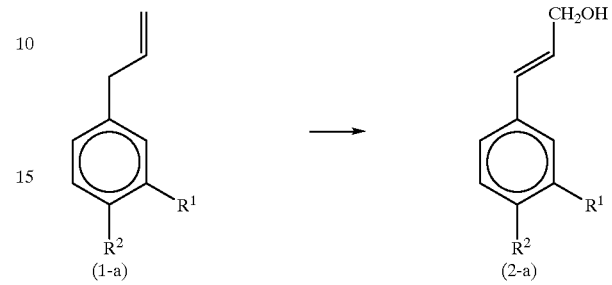

(Reaction Scheme B)

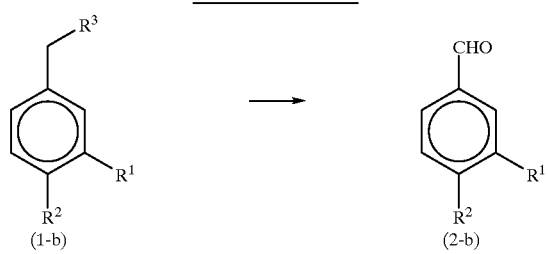

(Reaction Scheme C)

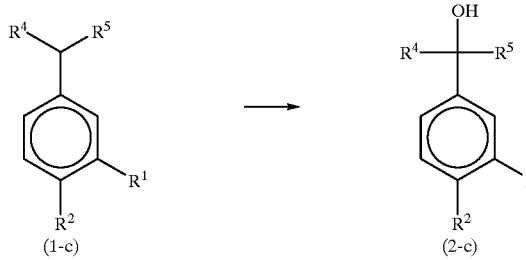

(Reaction Scheme C)

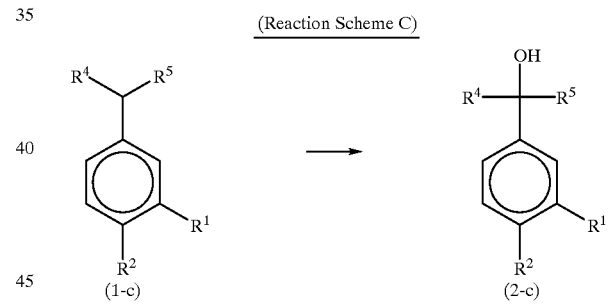

(Reaction Scheme C′)

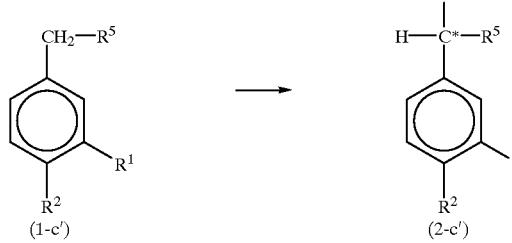

wherein $R^1$ represents a hydrogen atom or a hydroxyl or methoxy group; $R^2$ represents a hydroxyl or methoxy group; $R^3$ represents a hydrogen atom or a hydroxyl group; $R^4$ represents a hydrogen atom or a methyl group; and $R^5$ represents an alkyl group having 1 to 10 carbon atoms or an aminomethyl group;

(Reaction Scheme D)

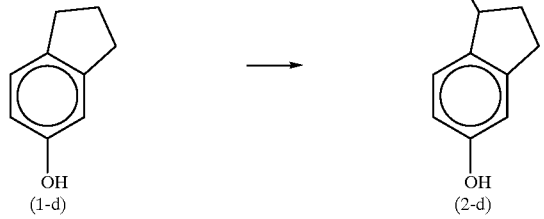

wherein $R^1$ represents a hydrogen atom or a hydroxyl or methoxy group; $R^2$ represents a hydroxyl or methoxy group; $R^3$ represents a hydrogen atom or a hydroxyl group; $R^4$ represents a hydrogen atom or a methyl group; and $R^5$ represents an alkyl group having 1 to 10 carbon atoms or an aminomethyl group.

3. The enzyme of claim 2 which catalyzes an asymmetry-inducing reaction represented by the reaction scheme C wherein $R^4$ is a hydrogen atom.

4. The enzyme of claim 2 wherein the strain belonging to the genus *Pseudomonas fluorescens* is *Pseudomonas fluorescens* E118 (FERM P-15185).

5. A method for preparing a 3-(p-hydroxyphenyl)-2-propenol derivative represented by the following general formula (2-a) starting from a p-allylphenol derivative represented by the following general formula (1-a) according to the reaction scheme A given below in the presence of water and an electron acceptor using an oxidoreductase having the following properties:

(1) Operation: The enzyme can produce coniferyl alcohol by moving the double bond at the α-position of eugenol (3) Affinity for Substrate: Michaelis constants of the enzyme for eugenol and phenazine methosulfate are 1.75 mM and 0.4 mM expressed in terms of substrate concentrations, respectively;

(4) Optimum pH: about 5.5;

(5) Optimum Growth Temperature: 50° C.;

(6) Stable pH Range: The enzyme is stable within the pH range of from 5 to 9 for treatment at 30° C. for 30 minutes;

(7) Effects of Various Kinds of Metal Salts on the Enzyme: The activity of the enzyme is considerably inhibited by salts of divalent iron, copper, silver and mercury;

(8) Effects of Various Kinds of Inhibitors: The activity of the enzyme is inhibited by p-(chloromercuri) benzoic acid and phenylhydrazine;

(9) Molecular Weight: The enzyme is a heterodimer having a molecular weight of 68,600 and consisting of an α-subunit having a molecular weight of 10,400 and a β-subunit having a molecular weight of 58,200.

to the position next thereto and adding a hydroxyl group to the α-position in the presence of water;

(2) Substrate Specificity: The enzyme acts on the compounds represented by the general formulas (1-a), (1-b), (1-c), (1-c') and (1-d) to give the compounds represented by the general formulas (2-a), (2-b), (2-c), (2-c') and (2-d) respectively;

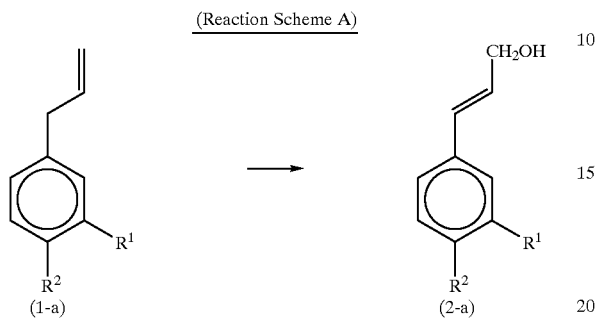

(Reaction Scheme A)

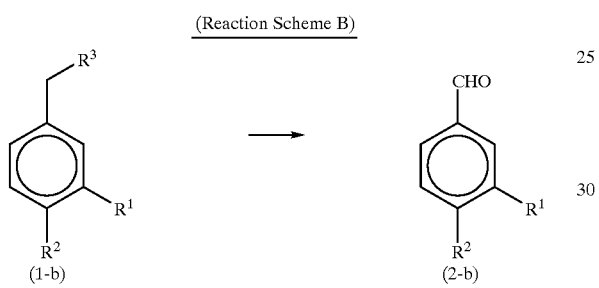

(Reaction Scheme B)

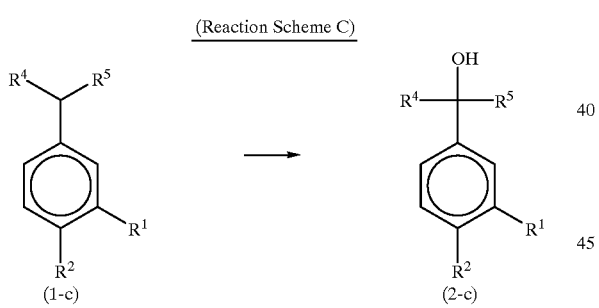

(Reaction Scheme C)

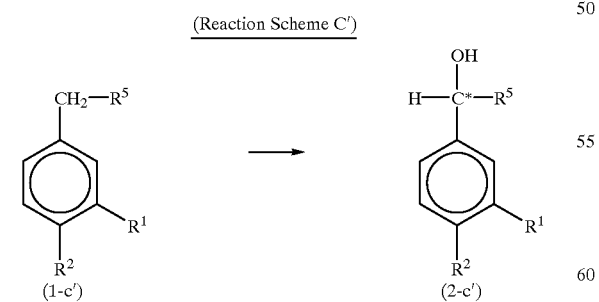

(Reaction Scheme C')

wherein $R^1$ represents a hydrogen atom or a hydroxyl or methoxy group; $R^2$ represents a hydlioxyl or methoxy group; $R^3$ represents a hydrogen atom or a hydroxyl group; $R^4$ represents a hydrogen atom or a methyl group; and $R^5$ represents an alkyl group having 1 to 10 carbon atoms or an aminomethyl group;

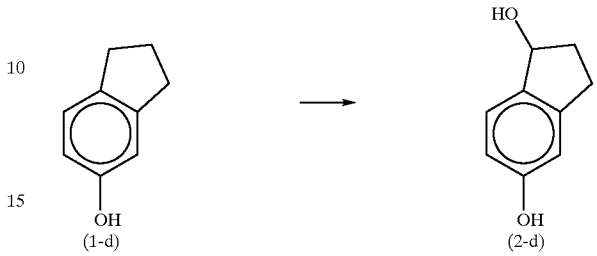

(Reaction Scheme D)

(3) Affinity for Substrate: Michaelis constants of the enzyme for eugenol and phenazine methosulfate are 1.75 mM and 0.4 mM expressed in terms of substrate concentrations, respectively;

(4) Optimum pH: about 5.5;

(5) Optimum Growth Temperature: 50° C.;

(6) Stable pH Range: The enzyme is stable within the pH range of from 5 to 9 for treatment at 30° C. for 30 minutes;

(7) Effects of Various Kinds of Metal Salts on the Enzyme: The activity of the enzyme is considerably inhibited by salts of divalent iron, copper, silver and mercury;

(8) Effects of Various Kinds of Inhibitors: The activity of the enzyme is inhibited by p-(chloromercuri) benzoic acid and phenylhydrazine;

(9) Molecular Weight: The enzyme is a heterodimer having a molecular weight of 68,600 and consisting of an α-subunit having a molecular weight of 10,400 and a β-subunit having a molecular weight of 58,200.

6. A method for preparing a p-hydroxybenzaldehyde derivative represented by the following general formula (2-b) starting from a p-hydroxytoluene derivative represented by the following general formula (1-b) according to the reaction scheme B given below in the presence of water and an electron acceptor using an oxidoreductase having the following properties:

(1) Operation: The enzyme can produce coniferyl alcohol by moving the double bond at the α-position of eugenol to the position next thereto and adding a hydroxyl group to the α-position in the presence of water;

(2) Substrate Specificity: The enzyme acts on the compounds represented by the general formulas (1-a), (1-b), (1-c), (1-c') and (1-d) to give the compounds represented by the general formulas (2-a), (2-b), (2-c), (2-c') and (2-d) respectively;

(Reaction Scheme A)

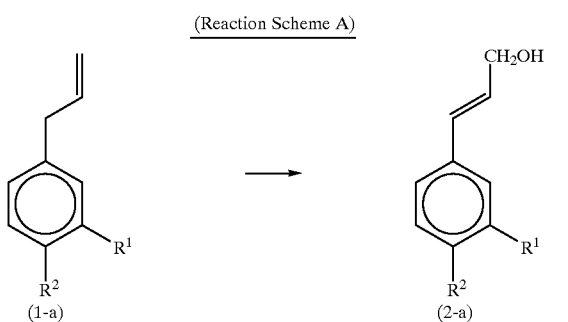

(Reaction Scheme B)

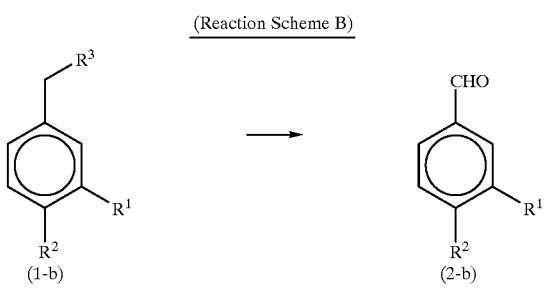

(Reaction Scheme C)

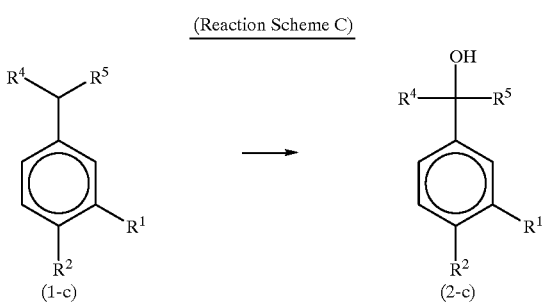

(Reaction Scheme C')

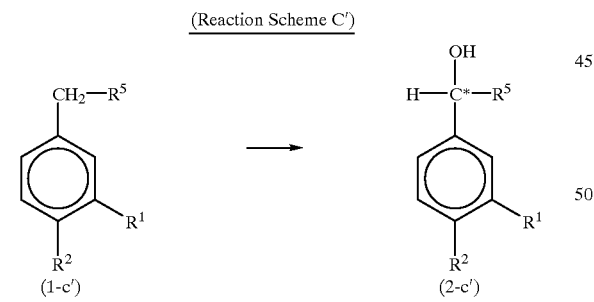

wherein $R^1$ represents a hydrogen atom or a hydroxyl or methoxy group; $R^2$ represents a hydxoxyl or methoxy group; $R^3$ represents a hydrogen atom or a hydroxyl group; $R^4$ represents a hydrogen atom or a methyl group; and $R^5$ represents an alkyl group having 1 to 10 carbon atoms or an aminomethyl group;

(Reaction Scheme D)

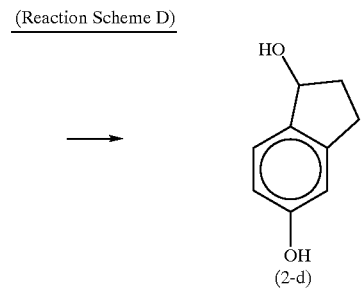

(3) Affinity for Substrate: Michaelis constants of the enzyme for eugenol and phenazine methosulfate are 1.75 mM and 0.4 mM expressed in terms of substrate concentrations, respectively;

(4) Optimum pH: about 5.5;

(5) Optimum Growth Temperature: 50° C.;

(6) Stable pH Range: The enzyme is stable within the pH range of from 5 to 9 for treatment at 30° C. for 30 minutes;

(7) Effects of Various Kinds of Metal Salts on the Enzyme: The activity of the enzyme is considerably inhibited by salts of divalent iron, copper, silver and mercury;

(8) Effects of Various Kinds of Inhibitors: The activity of the enzyme is inhibited by p-(chloromercuri) benzoic acid and phenylhydrazine;

(9) Molecular Weight: The enzyme is a heterodimer having a molecular weight of 68,600 and consisting of an α-subunit having a molecular weight of 10,400 and a β-subunit having a molecular weight of 58,200.

7. A method for preparing a p-hydroxybenzyl alcohol derivative represented by the following general formula (2-c) starting from a p-alkylphenol derivative represented by the following general formula (1-c) according to the reaction scheme C given below in the presence of water and an electron acceptor using an oxidoreductase having the following properties:

(1) Operation: The enzyme can produce coniferyl alcohol by moving the double bond at the α-position of eugenol to the position next thereto and adding a hydroxyl group to the α-position in the presence of water;

(2) Substrate Specificity: The enzyme acts on the compounds represented by the general formulas (1-a), (1-b), (1-c), (1-c') and (1-d) to give the compounds represented by the general formulas (2-a), (2-b), (2-c), (2-c') and (2-d) respectively;

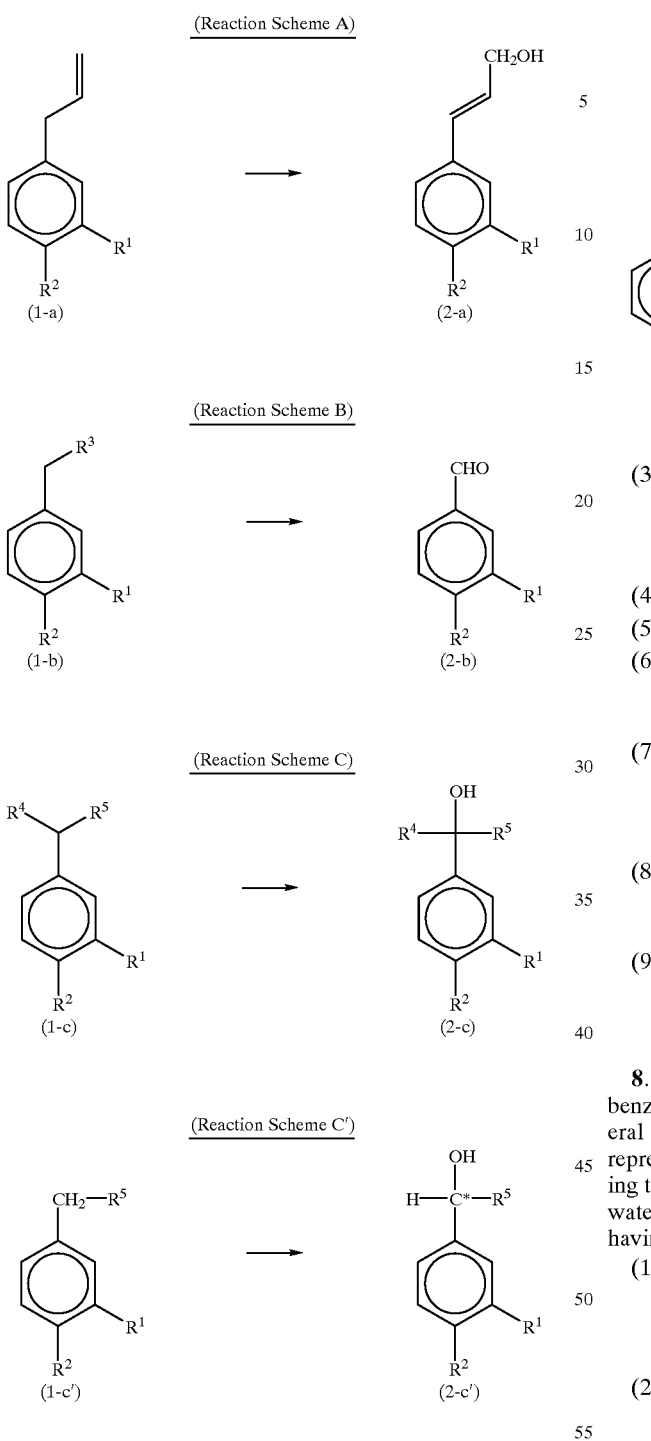

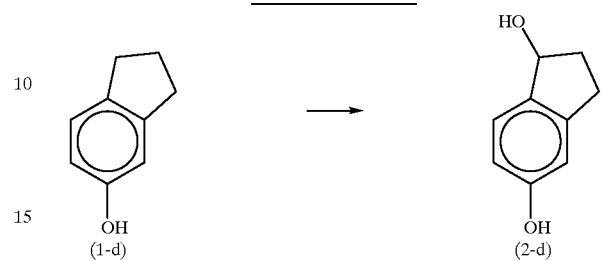

wherein $R^1$ represents a hydrogen atom or a hydroxyl or methoxy group; $R^2$ represents a hydroxyl or methoxy group; $R^3$ represents a hydrogen atom or a hydroxyl group; $R^4$ represents a hydrogen atom or a methyl group; and $R^5$ represents an alkyl group having 1 to 10 carbon atoms or an aminomethyl group;

(3) Affinity for Substrate: Michaelis constants of the enzyme for eugenol and phenazine methosulfate are 1.75 mM and 0.4 mM expressed in terms of substrate concentrations, respectively;

(4) Optimum pH: about 5.5;

(5) Optimum Growth Temperature: 50° C.;

(6) Stable pH Range: The enzyme is stable within the pH range of from 5 to 9 for treatment at 30° C. for 30 minutes;

(7) Effects of Various Kinds of Metal Salts on the Enzyme: The activity of the enzyme is considerably inhibited by salts of divalent iron, copper, silver and mercury;

(8) Effects of Various Kinds of Inhibitors: The activity of the enzyme is inhibited by p-(chloromercuri) benzoic acid and phenylhydrazine;

(9) Molecular Weight: The enzyme is a heterodimer having a molecular weight of 68,600 and consisting of an α-subunit having a molecular weight of 10,400 and a β-subunit having a molecular weight of 58,200.

8. A method for preparing an optically active hydroxybenzyl alcohol derivative represented by the following general formula (2-c') starting from an alkylphenol derivative represented by the following general formula (1-c') according to the reaction scheme C' given below in the presence of water and an electron acceptor using an oxidoreductase having the following properties:

(1) Operation: The enzyme can produce coniferyl alcohol by moving the double bond at the α-position of eugenol to the position next thereto and adding a hydroxyl group to the α-position in the presence of water;

(2) Substrate Specificity: The enzyme acts on the compounds represented by the general formulas (1-a), (1-b), (1-c), (1-c') and (1-d) to give the compounds represented by the general formulas (2-a), (2-b), (2-c), (2-c') and (2-d) respectively;

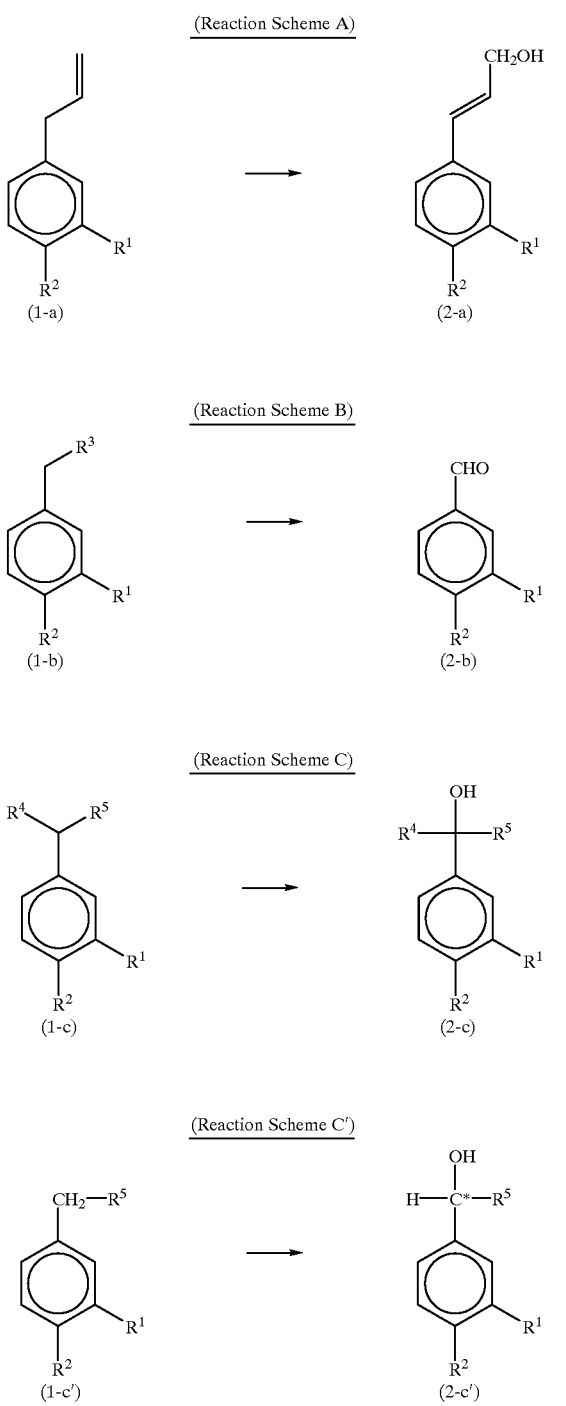

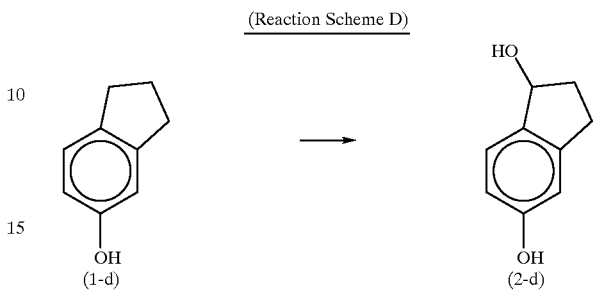

wherein $R^1$ represents a hydrogen atom or a hydroxyl or methoxy group; $R^2$ represents a hydroxyl or methoxy group; $R^3$ represents a hydrogen atom or a hydroxyl group; $R^4$ represents a hydrogen atom or a methyl group; and $R^5$ represents an alkyl group having 1 to 10 carbon atoms or an aminomethyl group;

(3) Affinity for Substrate: Michaelis constants of the enzyme for eugenol and phenazine methosulfate are 1.75 mM and 0.4 mM expressed in terms of substrate concentrations, respectively;

(4) Optimum pH: about 5.5;

(5) Optimum Growth Temperature: 50° C.;

(6) Stable pH Range: The enzyme is stable within the pH range of from 5 to 9 for treatment at 30° C. for 30 minutes;

(7) Effects of Various Kinds of Metal Salts on the Enzyme: The activity of the enzyme is considerably inhibited by salts of divalent iron, copper, silver and mercury;

(8) Effects of Various Kinds of Inhibitors: The activity of the enzyme is inhibited by p-(chloromercuri) benzoic acid and phenylhydrazine;

(9) Molecular Weight: The enzyme is a heterodimer having a molecular weight of 68,600 and consisting of an α-subunit having a molecular weight of 10,400 and a β-subunit having a molecular weight of 58,200.

9. A method for preparing the compound represented by the following general formula (2-d) starting from the compound represented by the following general formula (1-d) according to the reaction scheme D given below in the presence of water and an electron acceptor using an oxidoreductase having the following properties:

(1) Operation: The enzyme can produce coniferyl alcohol by moving the double bond at the α-position of eugenol to the position next thereto and adding a hydroxyl group to the α-position in the presence of water;

(2) Substrate Specificity: The enzyme acts on the compounds represented by the general formulas (1-a), (1-b), (1-c), (1-c') and (1-d) to give the compounds represented by the general formulas (2-a), (2-b), (2-c), (2-c') and (2-d) respectively;

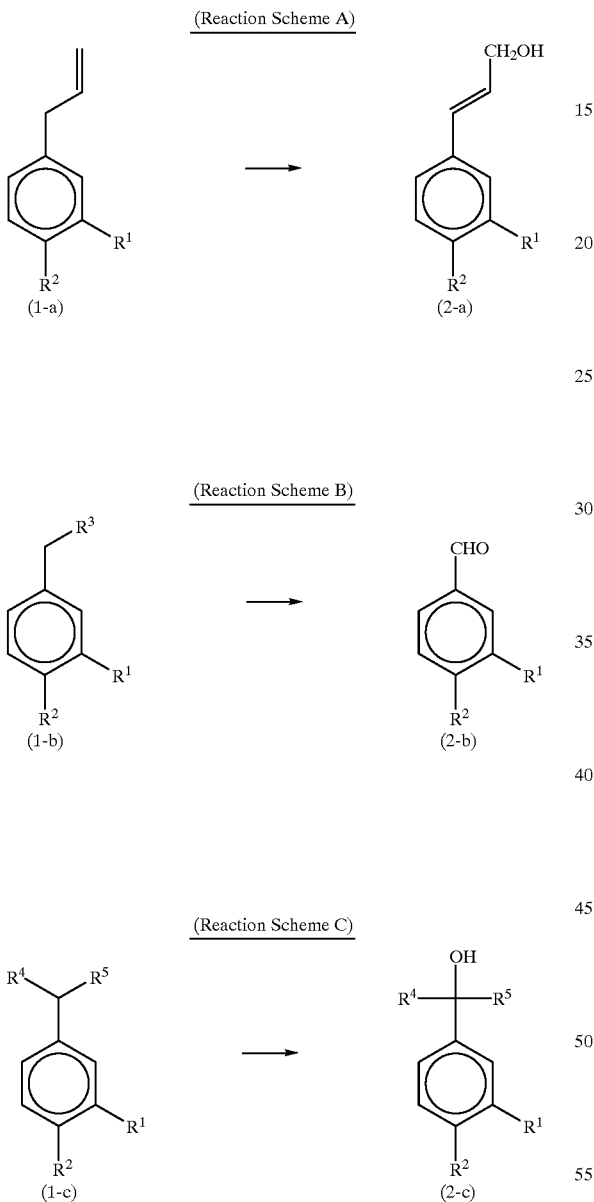

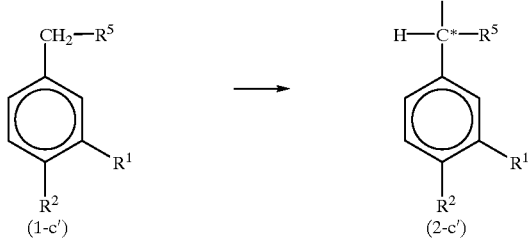

wherein $R^1$ represents a hydrogen atom or a hydroxyl or methoxy group; $R^2$ represents a hydroxyl or methoxy group; $R^3$ represents a hydrogen atom or a hydroxyl group; $R^4$ represents a hydrogen atom or a methyl group; and $R^5$ represents an alkyl group having 1 to 10 carbon atoms or an aminomethyl group;

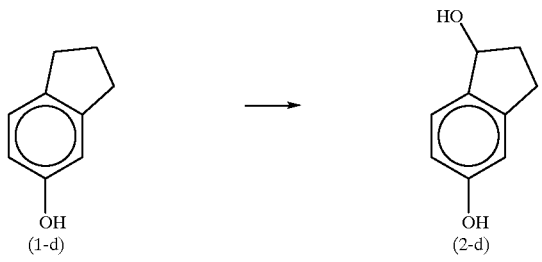

(3) Affinity for Substrate: Michaelis constants of the enzyme for eugenol and phenazine methosulfate are 1.75 mM and 0.4 mM expressed in terms of substrate concentrations, respectively;
(4) Optimum pH: about 5.5;
(5) Optimum Growth Temperature: 50° C.;
(6) Stable pH Range: The enzyme is stable within the pH range of from 5 to 9 for treatment at 30° C. for 30 minutes;
(7) Effects of Various Kinds of Metal Salts on the Enzyme: The activity of the enzyme is considerably inhibited by salts of divalent iron, copper, silver and mercury;
(8) Effects of Various Kinds of Inhibitors: The activity of the enzyme is inhibited by p-(chloromercuri) benzoic acid and phenylhydrazine;
(9) Molecular Weight: The enzyme is a heterodimer having a molecular weight of 68,600 and consisting of an α-subunit having a molecular weight of 10,400 and a β-subunit having a molecular weight of 58,200.

* * * * *